(12) United States Patent
Chen et al.

(10) Patent No.: US 12,397,081 B2
(45) Date of Patent: Aug. 26, 2025

(54) HYDROPHILIC FIBER MEMBRANE WITH SUSTAINED-RELEASE DRUG AND PREPARATION METHOD AND USE THEREOF

(71) Applicant: SHANGHAI RUIZHIKANG MEDICAL TECHNOLOGY CO., LTD., Shanghai (CN)

(72) Inventors: Xiaohong Chen, Shanghai (CN); Yubo Liu, Shanghai (CN); Honglei Zhou, Shanghai (CN); Wei Li, Shanghai (CN); Fengcang Ma, Shanghai (CN); Shaoli Fu, Shanghai (CN); Guosen Shao, Shanghai (CN); Haochen Wu, Shanghai (CN)

(73) Assignee: SHANGHAI RUIZHIKANG MEDICAL TECHNOLOGY CO., LTD., Shanghai (CN)

( * ) Notice: Subject to any disclaimer, the term of this patent is extended or adjusted under 35 U.S.C. 154(b) by 405 days.

(21) Appl. No.: 18/054,551

(22) Filed: Nov. 11, 2022

(65) Prior Publication Data

US 2024/0066177 A1    Feb. 29, 2024

(30) Foreign Application Priority Data

Aug. 24, 2022 (CN) .......................... 202211015909.5

(51) Int. Cl.
| | |
|---|---|
| A61L 15/26 | (2006.01) |
| A61L 15/20 | (2006.01) |
| A61L 15/28 | (2006.01) |
| A61L 15/32 | (2006.01) |
| A61L 15/44 | (2006.01) |
| D01F 1/10 | (2006.01) |
| D01F 8/02 | (2006.01) |

(52) U.S. Cl.
CPC .............. *A61L 15/26* (2013.01); *A61L 15/20* (2013.01); *A61L 15/28* (2013.01); *A61L 15/32* (2013.01); *A61L 15/44* (2013.01); *D01F 1/10* (2013.01); *D01F 8/02* (2013.01)

(58) Field of Classification Search
None
See application file for complete search history.

(56) References Cited

U.S. PATENT DOCUMENTS

2016/0220728 A1    8/2016    Adams et al.

FOREIGN PATENT DOCUMENTS

| CN | 106581779 A | * | 4/2017 |
| CN | 110464866 A | | 11/2019 |
| WO | 2012091636 A2 | | 7/2012 |

OTHER PUBLICATIONS

Abdullah, M. et al., "Core-Shell Fibers: Design, Roles, and Controllable Release Strategies in Tissue Engineering and Drug Delivery", Dec. 4, 2019, Polymers, 11(12):2008 (Year: 2019).*
Office Action mailed Jan. 19, 2023, in connection with Chinese Patent Application No. 202211015909.5, 16 pgs. (including translation).
Moradkhannejhad et al., "The effect of molecular weight and content of PEG on in vitro drug release of electrospun curcumin loaded PLA/PEG nanofibers", Journal of Drug Delivery Science and Technology, 2020, pp. 1-11.
"Pharmacopoeia of The People's Republic of China", Compiled by the National Pharmacopoeia Committee, 2015 Edition, Part IV, 42 pgs. (including translation).

* cited by examiner

*Primary Examiner* — Frederick F Krass
*Assistant Examiner* — Colman Welles
(74) *Attorney, Agent, or Firm* — Chiesa Shahinian & Giantomasi PC (57) ABSTRACT

The present disclosure provides a hydrophilic fiber membrane with a sustained-release drug, and belongs to the field of biological materials. The present disclosure provides a hydrophilic fiber membrane with a sustained-release drug, including a fiber with a core-shell structure, where a core of the fiber includes curcumin and a first spinnable polymer, and a shell of the fiber includes polyethylene glycol and a second spinnable polymer; and in the shell, the polyethylene glycol and the second spinnable polymer have a mass ratio of not greater than 1:12. In the present disclosure, the fiber membrane has a core-shell structure, the curcumin is provided in the core, and the shell prevents a rapid release of the curcumin in an early stage, thereby delaying a release rate of the curcumin to prevent the drug from forming a burst release in the early stage and causing toxic reactions.

11 Claims, 5 Drawing Sheets

HYDROPHILIC FIBER MEMBRANE WITH SUSTAINED-RELEASE DRUG AND PREPARATION METHOD AND USE THEREOF

CROSS REFERENCE TO RELATED APPLICATION

This patent application claims the benefit and priority of Chinese Patent Application No. 202211015909.5, filed Aug. 24, 2022; the disclosure of which is incorporated by reference herein in its entirety as part of the present application.

TECHNICAL FIELD

The present disclosure belongs to the field of biological materials, and in particular relates to a hydrophilic fiber membrane with a sustained-release drug and a preparation method and use thereof.

BACKGROUND

The skin, as the largest organ of the human body, is a main barrier against many external environmental stimuli in the body, including biological and chemical substances. Environmental stimuli or the influence of some force majeure factors may cause skin damages and wounds. For diabetic patients, if these wounds are not treated in time, exudates accumulated in the wounds can easily breed bacteria, thereby disrupting the immune system in human body.

Wound healing is an active repair process, and restorative or protective dressings can accelerate the healing and enhance the effectiveness of wound repair. Clinically, diabetic wounds are generally treated with debridement followed by medical gauze wrapping with drugs. Although this method is effective in treating diabetic wounds, the medical gauze has weak air permeability, high possibility in infection, and poor biocompatibility. More than that, hydrophobic medical gauze is difficult to absorb the exudates of the wounds. As a result, patients need to replace dressings frequently, leading to secondary injury and severe pain, as well as damages to newly formed skin tissues, thereby prolonging a healing period of the diabetic wounds.

Curcumin is a natural polyphenolic compound with a low cost, and has antibacterial properties and promotion of angiogenesis, granulation tissue formation, and collagen deposition; the curcumin has a desirable curative effect in wound treating and healing. However, curcumin has certain limited pharmacological effects and low oral availability. Moreover, as a polyphenolic compound, direct application of the curcumin may cause a high local concentration to produce a toxic reaction.

It may have a great significance in accelerating the healing of diabetic wounds and improving a wound repair effect by providing a dressing with hydrophilicity and sustained release of curcumin. However, since the release rate of a drug in fibers is mainly determined by an intrusion rate of water, and hydrophilic materials are prone to intrusion of water, such that the drug is generally completely released within a few hours, which cannot achieve the sustained release. Therefore, it is currently not possible to provide a dressing that has hydrophilicity and sustained release of curcumin.

SUMMARY

A purpose of the present disclosure is to provide a hydrophilic fiber membrane with a sustained-release drug and a preparation method and use thereof. The fiber membrane can realize the sustained-release of the drug, and has hydrophilic properties.

The present disclosure provides a hydrophilic fiber membrane with a sustained-release drug, including a fiber with a core-shell structure, where a core of the fiber includes curcumin and a first spinnable polymer, and a shell of the fiber includes polyethylene glycol and a second spinnable polymer; and in the shell, the polyethylene glycol and the second spinnable polymer have a mass ratio of not greater than 1:12.

Preferably, the first spinnable polymer and the second spinnable polymer each are one selected from the group consisting of cellulose acetate, polycaprolactone, polylactic acid, gelatin, and nylon.

Preferably, where in the core, the curcumin and the first spinnable polymer have a mass ratio of 1:(4-18).

Preferably, the core and the shell have a mass ratio of (13-21):13.

The present disclosure further provides a preparation method of the hydrophilic fiber membrane with a sustained-release drug, including the following steps:

conducting coaxial electrospinning on a core spinning solution and a shell spinning solution to obtain the hydrophilic fiber membrane with a sustained-release drug; where the core spinning solution includes the curcumin, the first spinnable polymer, and a first volatile organic solvent;

the shell spinning solution includes the polyethylene glycol, the second spinnable polymer, and a second volatile organic solvent; and in the shell spinning solution, the polyethylene glycol and the second spinnable polymer have a mass ratio of not greater than 1:12.

Preferably, the coaxial electrospinning is further conducted using a third volatile organic solvent with the core spinning solution and the shell spinning solution; when the coaxial electrospinning is conducted, the core spinning solution, the shell spinning solution, and the third volatile organic solvent are arranged from inside to outside sequentially.

Preferably, the core spinning solution has 1 g/L to 3 g/L of the curcumin and 12 g/L to 18 g/L of the first spinnable polymer by concentration.

Preferably, the first volatile organic solvent and the second volatile organic solvent each are a polar mixed solvent; and during the coaxial electrospinning, the first volatile organic solvent and the second volatile organic solvent each are added at a rate of 0.1 mL/h to 2 mL/h.

Preferably, during the coaxial electrospinning, the third volatile organic solvent is added at a rate of 0.1 mL/h to 2 mL/h.

The present disclosure further provides use of the hydrophilic fiber membrane with a sustained-release drug or a hydrophilic fiber membrane with a sustained-release drug prepared by the preparation method in preparation of a wound dressing.

The present disclosure provides a hydrophilic fiber membrane with a sustained-release drug, including a fiber with a core-shell structure, where a core of the fiber includes curcumin and a first spinnable polymer, and a shell of the fiber includes polyethylene glycol and a second spinnable polymer; and in the shell, the polyethylene glycol and the second spinnable polymer have a mass ratio of not greater than 1:12. In the fiber membrane, the fiber has a core-shell structure, and the curcumin is provided in the core, with a release rate depending on an intrusion rate of water; a higher intrusion rate of water into the fiber makes the curcumin in the fiber to leave a fiber matrix more rapidly with the diffusion of water molecules. The shell provides a barrier to the curcumin in the core, preventing the intrusion of moisture, thereby delaying a release rate of the drug to prevent the drug from forming a burst release in the early stage and causing toxic reactions; the polyethylene glycol in the shell provides the fiber with hydrophilic properties, thus giving the fiber membrane a strong ability to absorb exudates during the treatment of diabetic wounds. By controlling a ratio of the polyethylene glycol and the spinnable polymer in the shell, on a premise of ensuring hydrophilicity of the fiber membrane, the fiber membrane can also be prevented from being excessively hydrophilic to cause burst release of the curcumin in the core.

The present disclosure further provides a preparation method of the hydrophilic fiber membrane with a sustained-release drug. In the present disclosure, a non-spinnable third volatile organic solvent is used as an outermost layer, so as to prolong a volatilization time of the organic solvents in the spinning solution, such that the fiber is more stable and efficient during the preparation.

BRIEF DESCRIPTION OF THE DRAWINGS

FIG. 1-1 is a syringe containing a shell spinning solution;

FIG. 1-2 is a syringe containing a core spinning solution; FIG. 1-3 is a syringe containing a third volatile organic solvent; FIG. 1-4 is a high-voltage electrostatic generating device; FIG. 1-5 is a ground connection; FIG. 1-6 is a collection device; FIG. 1-7 is an injection pump propulsion device; and FIG. 1-8 is a three-stage coaxial spinning nozzle;

DETAILED DESCRIPTION

The present disclosure provides a hydrophilic fiber membrane with a sustained-release drug, including a fiber with a core-shell structure, where a core of the fiber includes curcumin and a first spinnable polymer, and a shell of the fiber includes polyethylene glycol and a second spinnable polymer; and in the shell, the polyethylene glycol and the second spinnable polymer have a mass ratio of not greater than 1:12.

In the present disclosure, the fiber with a core-shell structure preferably has a bubble-type core-shell structure, and a composition of bubbles is preferably the same as that of the shell. There is no special limitation on a position of the bubbles; specifically, the beads may be in the core, or between the core and the shell. The bubble-type core-shell structure is more conducive to the sustained release of the drug.

In the present disclosure, the first spinnable polymer and the second spinnable polymer each are preferably one selected from the group consisting of cellulose acetate, polycaprolactone, polylactic acid, gelatin, and nylon. In the core, the curcumin and the first spinnable polymer have a mass ratio of preferably 1:(4-18), more preferably 1:(5-12), and further more preferably 1:(8-10). In the shell, the polyethylene glycol and the second spinnable polymer have a mass ratio of not greater than 1:12, preferably (0.5-0.8):12. The core and the shell have a mass ratio of preferably (13-21):13. In the hydrophilic fiber membrane, the fiber has a diameter of preferably 210 nm to 870 nm, more preferably 300 nm to 810 nm, and further more preferably 340 nm to 710 nm. The shell has a thickness of preferably 86 nm to 140 nm, more preferably 90 nm to 120 nm, and further more preferably 100 nm to 110 nm. The core has a thickness of preferably 124 nm to 730 nm, more preferably 210 nm to 690 nm, and further more preferably 240 nm to 600 nm.

In the fiber membrane, the fiber has a core-shell structure, and the curcumin is provided in the core, with a release rate depending on an intrusion rate of water; a higher intrusion rate of water into the fiber makes the curcumin in the fiber to leave a fiber matrix more rapidly with the diffusion of water molecules. The shell provides a barrier to the curcumin in the core, preventing the intrusion of moisture, thereby delaying a release rate of the drug to prevent the drug from forming a burst release in the early stage and causing toxic reactions; the polyethylene glycol in the shell provides the fiber with hydrophilic properties, thus giving the fiber membrane a strong ability to absorb exudates during the treatment of diabetic wounds. By controlling a ratio of the polyethylene glycol and the spinnable polymer in the shell, on a premise of ensuring hydrophilicity of the fiber membrane, the fiber membrane can also be prevented from being excessively hydrophilic to cause burst release of the curcumin in the core.

The present disclosure further provides a preparation method of the hydrophilic fiber membrane with a sustained-release drug, including the following steps:
conducting coaxial electrospinning on a core spinning solution and a shell spinning solution to obtain the hydrophilic fiber membrane with a sustained-release drug; where
the core spinning solution includes the curcumin, the first spinnable polymer, and a first volatile organic solvent;
the shell spinning solution includes the polyethylene glycol, the second spinnable polymer, and a second volatile organic solvent; and in the shell spinning solution, the polyethylene glycol and the second spinnable polymer have a mass ratio of not greater than 1:12.

In the present disclosure, coaxial electrospinning is conducted on the core spinning solution and the shell spinning solution to obtain the hydrophilic fiber membrane with a sustained-release drug. The first volatile organic solvent is preferably a polar mixed solvent selected from the group consisting of preferably a mixed solution of acetone, ethanol, and N,N-dimethylacetamide, a mixed solution of the acetone and the ethanol, a mixed solution of the acetone and the N,N-dimethylacetamide, and a mixed solution of the acetone and methanol. In the mixed solution, the acetone, the ethanol, and the N,N-dimethylacetamide have a volume ratio of preferably 4:1:1 or 3:2:1; when the polar mixed solvent is the mixed solution of the acetone and the ethanol, the mixed solution of the acetone and the N,N-dimethylacetamide, and the mixed solution of the acetone and the methanol, the mixed solution has preferably 50% to 99% of the acetone by volume content. The core spinning solution has preferably 1 g/L to 3 g/L, more preferably 2 g/L to 2.5 g/L of the curcumin, and preferably 12 g/L to 18 g/L, more preferably 15 g/L to 16 g/L of the first spinnable polymer by concentration. A preparation method of the core spinning solution preferably includes: mixing the curcumin, the first spinnable polymer, and the first volatile organic solvent to obtain the core spinning solution. There is no special limitation on the mixing, as long as the solution can be uniformly mixed until clear by adopting schemes well known to those skilled in the art. Specifically, in an example, the mixing is conducted by magnetic stirring at 60° C. for 2 h on a constant-temperature water bath.

In the present invention, the shell spinning solution includes the polyethylene glycol, the second spinnable polymer, and the second volatile organic solvent. The second volatile organic solvent is preferably the same as the first volatile organic solvent. The shell spinning solution has 1 g/L of the polyethylene glycol and preferably 12 g/L of the second spinnable polymer by concentration. A preparation method of the shell spinning solution preferably includes: mixing the curcumin, the second spinnable polymer, and the second volatile organic solvent to obtain the shell spinning solution. There is no special limitation on the mixing, as long as the solution can be uniformly mixed by adopting schemes well known to those skilled in the art. Specifically, in an example, the mixing is conducted by magnetic stirring at 60° C. for 2 h on a constant-temperature water bath.

During the coaxial electrospinning, a spinning nozzle and a collector have a spacing of preferably 15 cm to 20 cm, more preferably 16 cm to 18 cm. The coaxial electrospinning is conducted at preferably 25° C. to 40° C., more preferably 30° C. to 35° C. with an environmental humidity of preferably 30% to 60%, more preferably 40% to 50%, and further more preferably 45 to 48%. The coaxial electrospinning is conducted at a voltage of preferably 10 kV to 11 kV, more preferably 10.5 kV to 10.8 kV. Preferably, when droplets at the spinning nozzle of the coaxial electrospinning are gradually formed and stabilized, the voltage of the coaxial electrospinning is slowly increased to 10 kV to 11 kV; after an entire electrospinning process is stable, a new collector is replaced to start collecting the nanofibers. There is no special limitation on the collector, and collectors known to those skilled in the art can be selected. Specifically, in an example, the collector is an aluminum foil.

In the present disclosure, before the coaxial electrospinning, the core spinning solution and the shell spinning solution are preferably loaded into two syringes and then placed on two propelling pumps, respectively. When the coaxial electrospinning is conducted, the core spinning solution and the shell spinning solution each are added at a rate of preferably 0.1 mL/h to 2 mL/h, more preferably 0.5 mL/h to 1.5 mL/h, and further more preferably 1 mL/h to 1.2 mL/h. The syringe containing the core spinning solution is preferably placed laterally and connected to the spinning nozzle through a silicone hose, and the syringe containing the shell spinning solution is preferably placed vertically and directly connected to the spinning nozzle. During the coaxial electrospinning, the core spinning solution and the shell spinning solution are simultaneously ejected from the nozzle. Under the action of a propelling pump, the core spinning solution and the shell spinning solution are aggregated at a coaxial spinning nozzle. Under the action of a high-voltage static electricity, the aggregated solution is drawn into silk, and organic solvents in the core spinning solution and the shell spinning solution volatilizes rapidly; meanwhile, the first spinnable polymer as well as the curcumin, the second spinnable polymer, and the polyethylene glycol are rapidly drawn to form the fiber with a core-shell structure. The curcumin is stored in a core layer of the fiber; and a shell layer of the fiber, as a hydrophilic layer, is prepared from the second spinnable polymer and the polyethylene glycol. The hydrophilic shell layer provides hydrophilicity to the nanofibers, and provides a strong ability to absorb exudates when being used as a wound dressing; in addition, an appropriate amount of the polyethylene glycol in the shell can further prevent an early rapid release of the curcumin in the form of a barrier.

In the present disclosure, the coaxial electrospinning is further conducted preferably using a third volatile organic solvent with the core spinning solution and the shell spinning solution. When the coaxial electrospinning is conducted, the core spinning solution, the shell spinning solution, and the third volatile organic solvent are preferably arranged from inside to outside sequentially. The third volatile organic solvent is preferably the same as the first volatile organic solvent. The non-spinnable third volatile organic solvent is used as an outermost layer, so as to prolong a volatilization time of the organic solvents in the spinning solution, such that the fiber is more stable and efficient during the preparation without fiber breakage. The coaxial electrospinning is conducted using preferably a three-stage coaxial spinning nozzle.

In the present disclosure, when the third volatile organic solvent is used, before the coaxial electrospinning, the core spinning solution, the shell spinning solution, and the third volatile organic solvent are preferably loaded into three syringes and placed on three propelling pumps, respectively. During the coaxial electrospinning, the third volatile organic solvent is added at a rate of preferably 0.1 mL/h to 2 mL/h, more preferably 0.5 mL/h to 1.5 mL/h, and further more preferably 1 mL/h to 1.2 mL/h. The syringe containing the core spinning solution and the syringe containing the third volatile organic solvent are preferably placed laterally and connected to the spinning nozzle through a silicone hose, and the syringe containing the shell spinning solution is preferably placed vertically and directly connected to the spinning nozzle. During the coaxial electrospinning, the core spinning solution, the shell spinning solution, and the third volatile organic solvent are simultaneously ejected from the nozzle. Under the action of a propelling pump, the core spinning solution, the shell spinning solution, and the third volatile organic solvent are aggregated at a three-stage coaxial spinning nozzle. Under the action of a high-voltage static electricity, the aggregated solution is drawn into silk, and organic solvents in the core spinning solution and the shell spinning solution, and the third volatile organic solvent volatilizes rapidly; meanwhile, the first spinnable polymer as well as the curcumin, the second spinnable polymer, and the polyethylene glycol are rapidly drawn to form the fiber with a core-shell structure.

Figure 1:
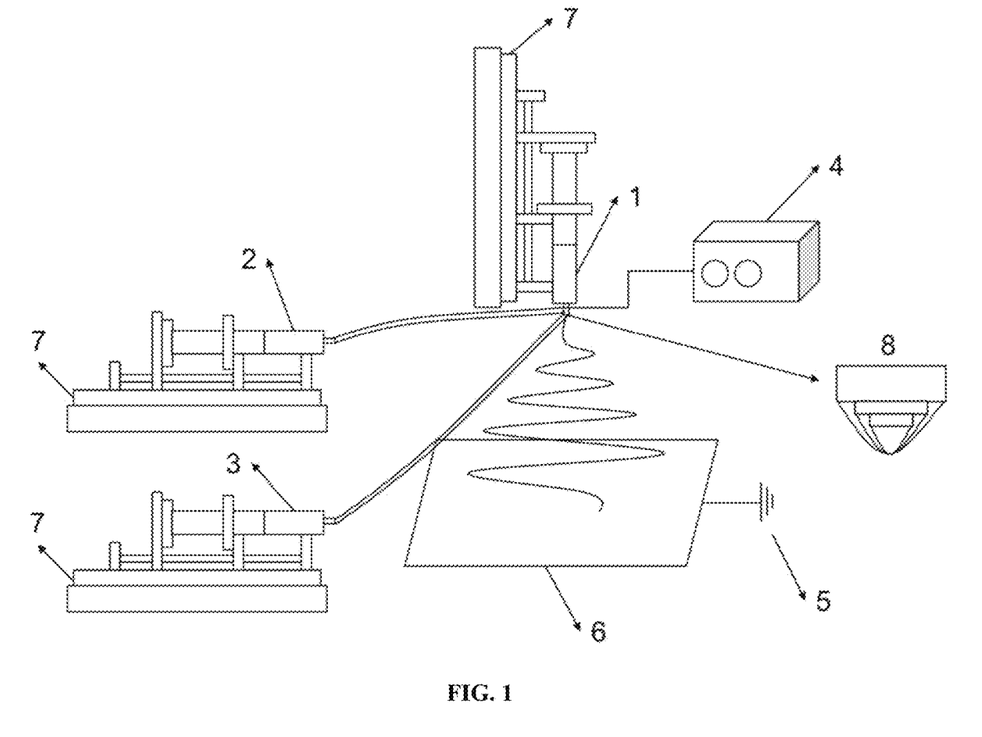
FIG. 1 shows a schematic structural diagram of an coaxial electrospinning device used in examples of the present disclosure; where

In the present disclosure, there is no special limitation on a device for the coaxial electrospinning, and devices well known to those skilled in the art may be used. Specifically, in an example, a device described in FIG. 1 is used. In FIG. 1, FIG. 1-1 is a syringe containing a shell spinning solution; FIG. 1-2 is a syringe containing a core spinning solution; FIG. 1-3 is a syringe containing a third volatile organic solvent; FIG. 1-4 is a high-voltage electrostatic generating device; FIG. 1-5 is a ground connection; FIG. 1-6 is a collection device; FIG. 1-7 is an injection pump propulsion device; and FIG. 1-8 is a three-stage coaxial spinning nozzle.

The present disclosure further provides use of the hydrophilic fiber membrane with a sustained-release drug or a hydrophilic fiber membrane with a sustained-release drug prepared by the preparation method in preparation of a wound dressing, preferably in preparation of a dressing for diabetic wounds.

In order to further illustrate the present disclosure, the hydrophilic fiber membrane with a sustained-release drug and the preparation method and the use thereof provided by the present disclosure are described in detail below with reference to the accompanying drawings and examples, but the accompanying drawings and the examples should not be construed as limiting the protection scope of the present disclosure.

Example 1

0.72 g of cellulose acetate and 0.12 g of curcumin were added to a 30 mL transparent glass bottle, 6 mL of a mixed solvent solution was pipetted into the glass bottle with a pipette, where the mixed solvent included acetone, ethanol, and N,N-dimethylacetamide at a volume ratio of 4:1:1; a magnetic rotor was added to the glass bottle and a bottle cap was tightened, an obtained mixture was stirred in a constant-temperature water bath at 60° C. for 2 h to obtain a clear core spinning solution. The core spinning solution had 12 g/L of the cellulose acetate and 2 g/L of the curcumin by concentration.

0.72 g of the cellulose acetate and 0.06 g of polyethylene glycol were placed in 6 mL of the mixed solvent, and stirred at 60° C. for 2 h on the constant-temperature water bath to obtain a shell spinning solution. The shell spinning solution had 12 g/L of the cellulose acetate and 1 g/L of the polyethylene glycol by concentration.

4 mL of the acetone, 1 mL of the ethanol, and 1 mL of the N,N-dimethylacetamide were pipetted into a 30 mL transparent glass bottle with a pipette, and shaken evenly to obtain a third volatile organic solvent.

A spinning environment was set up at 35° C. with a humidity of 45%. A multi-fluid spinning device was shown in FIG. 1. The core spinning solution, the shell spinning solution, and the third volatile organic solvent are loaded into plastic syringes, respectively, which were then fixed on a syringe pump propulsion device 7; where the plastic syringe containing the shell spinning solution was placed vertically at position 1 and then directly connected to a three-stage coaxial spinning nozzle 8, and the plastic syringes containing the core spinning solution and the third volatile organic solvent were placed at positions 2 and 3, respectively, and then connected to the three-stage coaxial spinning nozzle 8 through a hose. An aluminum foil paper 6 was subjected to ground connection 5, a spacing was set to 15 cm between the three-stage coaxial spinning nozzle 8 and the aluminum foil paper 6 as a receiving device, and multi-fluid electrospinning was started.

The core spinning solution, the shell spinning solution, and the third volatile organic solvent were subjected to coaxial electrospinning at a rate of 1.0 mL/h separately. When the core spinning solution, the shell spinning solution, and the third volatile organic solvent each flowed out stably from the three-stage coaxial spinning nozzle 8, a high-voltage electrostatic generator was turned on and slowly adjusted to a voltage of 10 kV. A fiber membrane was obtained after the multi-fluid electrospinning was continued for a period of time. In the shell of the fiber, the polyethylene glycol and the cellulose acetate had a mass ratio of 1:12.

Figure 2:
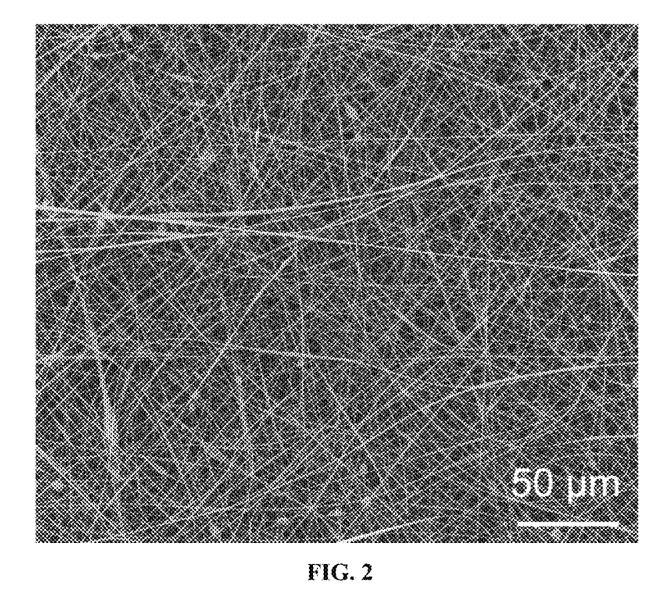
FIG. 2 shows a SEM image of a fiber membrane prepared in Example 1.

An electron microscope analysis was conducted on the fiber membrane prepared in Example 1, and results were shown in FIG. 2. It was seen from FIG. 2 that the fiber prepared in Example 1 had a diameter of 340 nm to 710 nm, and had a cylindrical shape with a certain number of beads.

Figure 5:
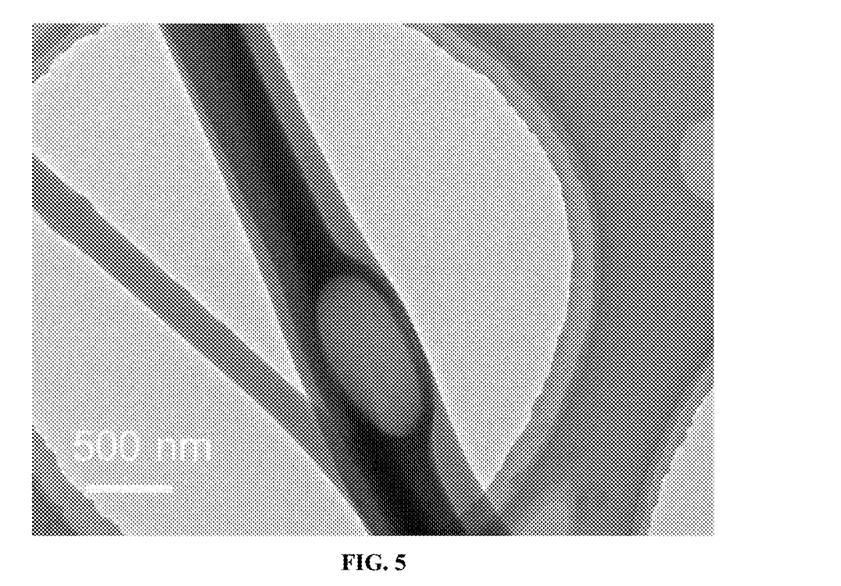
FIG. 5 shows a TEM image of the fiber membrane prepared in Example 1.

The fiber prepared in Example 1 was analyzed by TEM, and results were shown in FIG. 5. It was seen from FIG. 5 that the fiber prepared in Example 1 had a core-shell structure, and an "oval" part inside the fiber corresponded to an internal structure of the fiber bead in FIG. 2. This was because incomplete stretching of the spinning solution by the electric field during the electrospinning produced this unique "bubble-type" core-shell structure, which was more conducive to the sustained release of drugs. The fiber of Example 1 had a shell thickness of 100 nm to 110 nm and a core thickness of 240 nm to 600 nm.

Comparative Example 1

This example differed from Example 1 only in that: 0.18 g of the polyethylene glycol was used (the polyethylene glycol in the shell spinning solution had a concentration of 3 g/L), and the coaxial electrospinning was conducted at a voltage of 10.5 kV.

Figure 3:
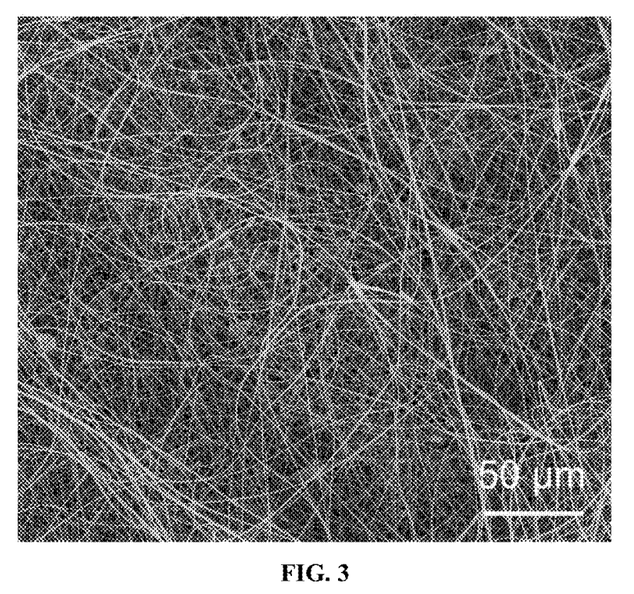
FIG. 3 shows a SEM image of a fiber membrane prepared in Example 2.

An electron microscope analysis was conducted on the fiber membrane prepared in Comparative Example 1, and results were shown in FIG. 3. It was seen from FIG. 3 the fiber prepared in Comparative Example 1 had a diameter of 300 nm to 810 nm, and had a cylindrical shape with a certain number of beads. The fiber of Comparative Example 1 had a shell thickness of 90 nm to 120 nm and a core thickness of 210 nm to 690 nm.

Comparative Example 2

This example differed from Example 1 only in that: 0.36 g of the polyethylene glycol was used (the polyethylene glycol in the shell spinning solution had a concentration of 6 g/L), and the coaxial electrospinning was conducted at a voltage of 11 kV.

Figure 4:
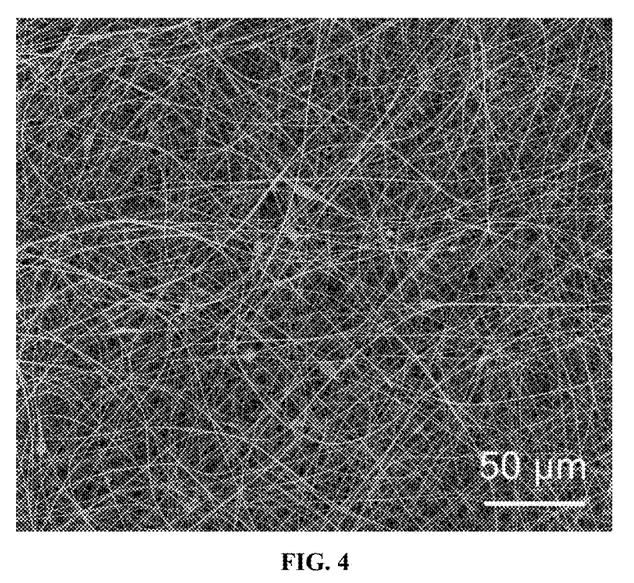
FIG. 4 shows a SEM image of a fiber membrane prepared in Example 3.

An electron microscope analysis was conducted on the fiber membrane prepared in Comparative Example 2, and results were shown in FIG. 4. It was seen from FIG. 4 the fiber prepared in Comparative Example 2 had a diameter of 210 nm to 870 nm, and had a cylindrical shape with a certain number of beads. The fiber of Comparative Example 2 had a shell thickness of 86 nm to 140 nm and a core thickness of 124 nm to 730 nm.

FIG. 2 to FIG. 4 were SEM images of the nanofibers prepared in Example 1 and Comparative Examples 1 to 2, respectively, showing that the three kinds of fibers each had a cylindrical shape with a certain number of beads.

The fiber membranes prepared in Example 1 and Comparative Examples 1 to 2 each were cut into a rectangle of 20 mm×60 mm, a water contact angle was tested using an interfacial tension tester for each fiber membrane, the measurement was repeated 3 times, and a mean and a standard deviation were calculated. The results were shown in FIG. 6 to FIG. 8, and results corresponding to FIG. 6 to FIG. 8 were shown in Table 1.

TABLE 1

Test results of hydrophilic properties of fiber membranes of Example 1 and Comparative Examples 1 to 2

|  | 0 s | 5 s | 10 s | 20 s | 120 s | 130 s | 140 s |
|---|---|---|---|---|---|---|---|
| Example 1 | 122.47 ± 1.75 | — | — | — | 85.28 ± 3.56 | 30.96 ± 5.08 | 17.70 ± 4.90 |
| Comparative Example 1 | 101.38 ± 1.42 | 33.24 ± 2.41 | 29.33 ± 3.64 | 20.12 ± 6.03 | — | — | — |
| Comparative Example 2 | 85.52 ± 1.99 | 24.38 ± 4.20 | 13.28 ± 2.73 | 5.37 ± 2.15 | — | — | — |

Figure 6:
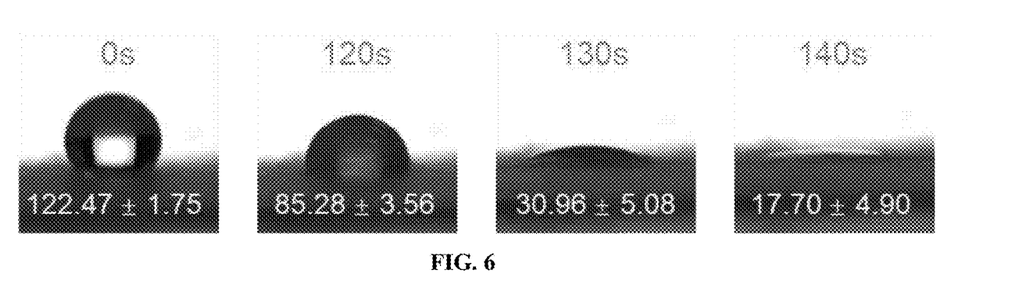
FIG. 6 shows a water contact angle diagram of the fiber membrane prepared in Example 1.
Figure 7:
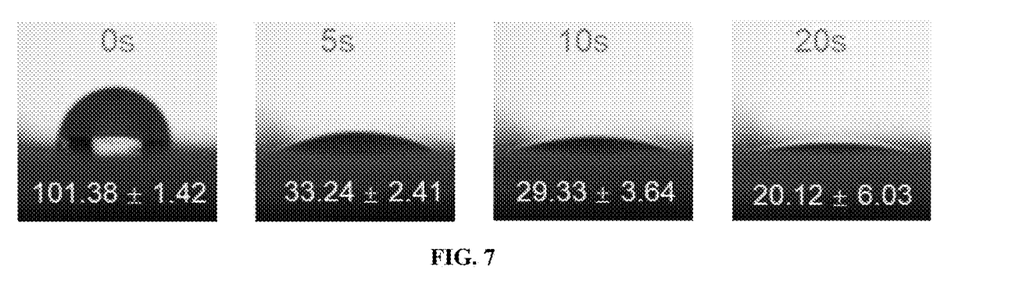
FIG. 7 shows a water contact angle diagram of the fiber membrane prepared in Example 2.
Figure 8:
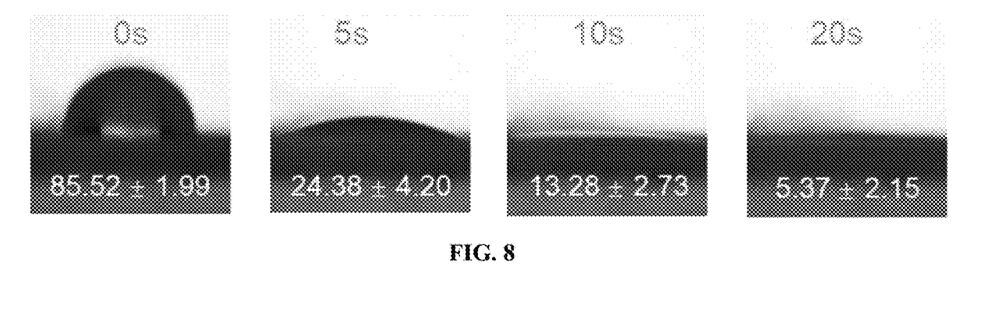
FIG. 8 shows a water contact angle diagram of the fiber membrane prepared in Example 3.

It was seen from FIG. 5 to FIG. 7 and Table 2 that the nanofibers prepared in Example 1 and Comparative Examples 1 to 2 each had desirable hydrophilicity; in particular, the nanofiber membranes prepared in Comparative Examples 1 to 2 had better hydrophilic properties than that prepared in Example 1.

Figure 9:
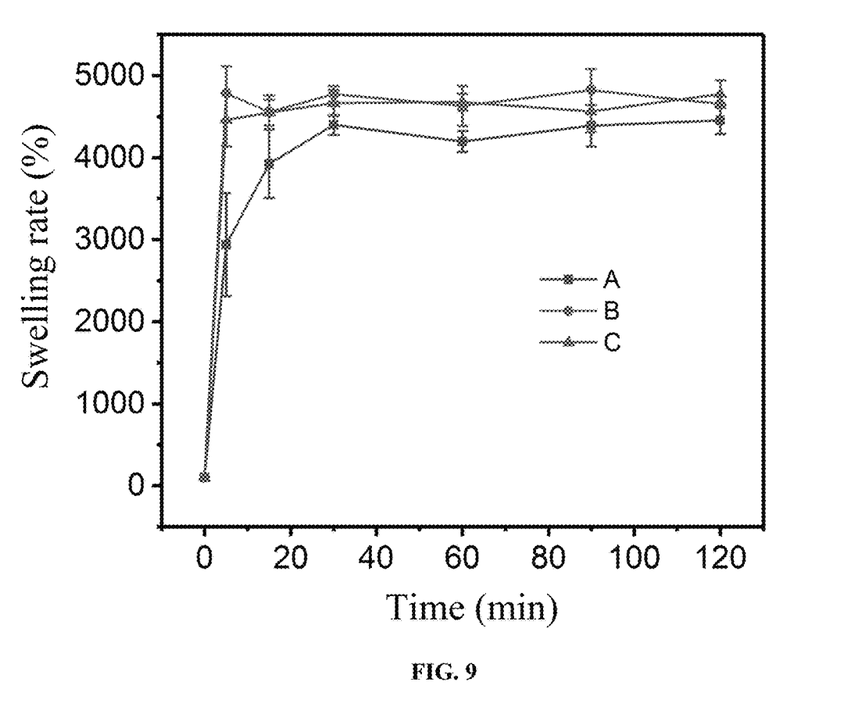
FIG. 9 shows swelling properties of the nanofiber membranes prepared in Examples 1 to 3.

0.02 g of the fibers prepared in Example 1 and Comparative Examples 1 to 2 were placed in 500 ml of a PBS buffer, and the fibers were taken out at regular intervals and weighed; a swelling property of the fiber was evaluated according to a mass change of the fiber after water absorption, the mass change was measured 3 times, and a mean and a standard deviation were calculated. The results were shown in FIG. 9, and results corresponding to FIG. 9 were shown in Table 2. FIG. 9A, FIG. 9B, and FIG. 9C in FIG. 9 represented the fibers prepared in Example 1 and Comparative Examples 1 to 2, respectively.

TABLE 2

Test results of swelling properties of fiber membranes of Example 1 and Comparative Examples 1 to 2

| | Swelling rate/% | | | | | | |
|---|---|---|---|---|---|---|---|
| | 0 min | 5 min | 15 min | 30 min | 60 min | 90 min | 120 min |
| Example 1 | 100% | 2937% ± 629% | 3924% ± 419% | 4400% ± 121% | 4198% ± 127% | 4389% ± 254% | 4456% ± 168% |
| Comparative Example 1 | 100% | 4786% ± 324% | 4555% ± 206% | 4775% ± 93% | 4631% ± 243% | 4823% ± 258% | 4654% ± 68% |
| Comparative Example 2 | 100% | 4459% ± 324% | 4550% ± 158% | 4665% ± 155% | 4675% ± 102% | 4564% ± 256% | 4775% ± 167% |

It was seen from FIG. 9 and Table 2 that the three fibers had swelling properties that were not much different, and each had a desirable potential for absorbing wound exudates.

According to a pulp method experiment of the 2015 version of the Chinese Pharmacopoeia, a drug release performance test was conducted on each of the fibers prepared in Example 1 and Comparative Examples 1 to 2, the test was repeated 3 times, and a mean and a standard deviation were calculated. The results were shown in FIG. 10, and results corresponding to FIG. 10 were shown in Table 3.

TABLE 3

Test results of drug release properties of fiber membranes of Example 1 and Comparative Examples 1 to 2

| Drug release efficiency | Example 1 | Comparative Example 1 | Comparative Example 2 |
|---|---|---|---|
| 0 h | 0% | 0% | 0% |
| 0.5 h | 8.72% ± 0.51% | 21.40% ± 1.54% | 22.06% ± 3.59% |
| 1 h | 10.45% ± 1.31% | 24.91% ± 0.85% | 27.01% ± 1.84% |
| 2 h | 14.49% ± 1.94% | 34.05% ± 1.00% | 40.57% ± 3.74% |
| 4 h | 25.69% ± 2.53% | 49.64% ± 1.22% | 53.21% ± 7.25% |
| 8 h | 41.25% ± 10.19% | 73.51% ± 3.66% | 78.98% ± 7.05% |
| 12 h | 54.78% ± 16.25% | 84.89% ± 2.13% | 83.32% ± 6.19% |
| 24 h | 70.25% ± 14.52% | 85.75% ± 3.10% | 82.97% ± 6.28% |
| 36 h | 76.20% ± 10.88% | 84.56% ± 2.93% | 82.38% ± 6.47% |
| 48 h | 79.21% ± 8.45% | 84.21% ± 3.10% | 80.76% ± 6.24% |
| 60 h | 83.46% ± 6.99% | — | — |
| 72 h | 85.52% ± 5.32% | — | — |
| 84 h | 87.10% ± 3.71% | — | — |
| 96 h | 87.54% ± 2.98% | — | — |

Figure 10:
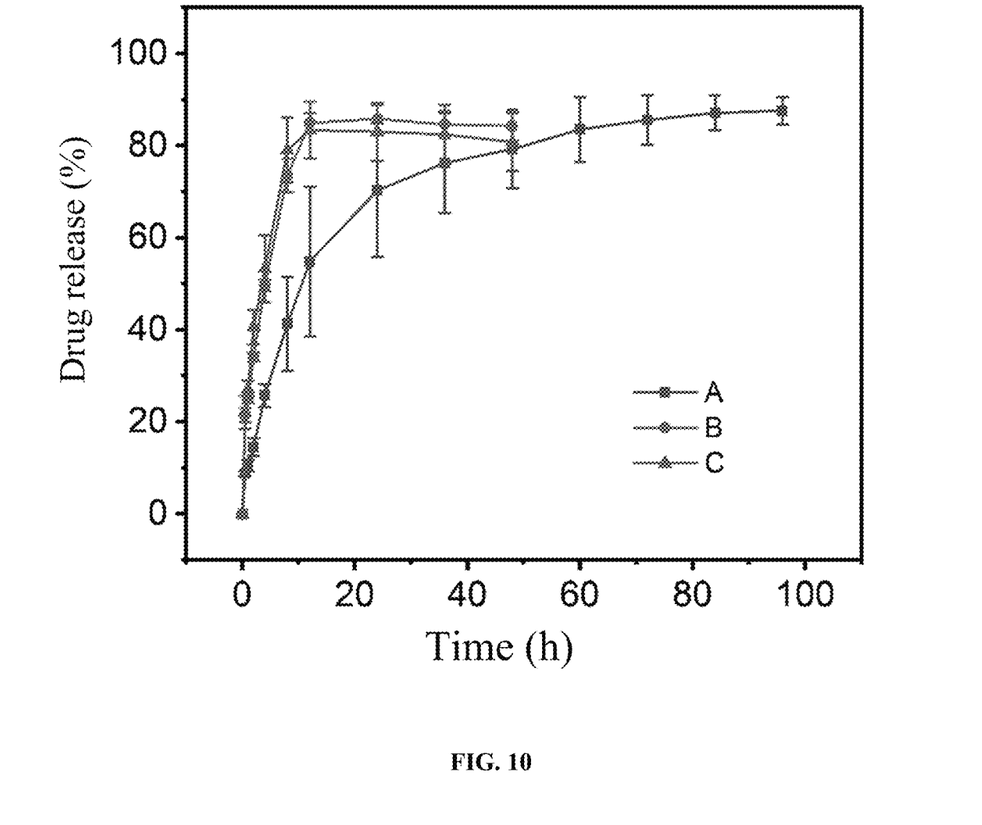
FIG. 10 shows drug release states of the nanofiber membranes prepared in Examples 1 to 3.

It was seen from FIG. 10 and Table 3 that the fiber membrane of Example 1 had an obvious sustained-release effect; while the fiber membranes of Comparative Examples 1 to 2 were not particularly helpful for the sustained-release of drugs, because the material was excessively hydrophilic and might accelerate the release of the drugs. Therefore, the nanofiber prepared in Example 1 is a preferred example of the hydrophilic diabetic wound dressing with a sustained-release drug in the present disclosure. The nanofiber can well absorb exudates and has the sustained release of drugs, which are expected to accelerate the healing of diabetic wounds in a synergistic effect.

Although the present disclosure is described in detail in conjunction with the foregoing examples, they are only a part of, not all of, the examples of the present disclosure. Other examples can be obtained based on these examples without creative efforts, and all of these examples shall fall within the protection scope of the present disclosure.

What is claimed is:

1. A hydrophilic fiber membrane with a sustained-release drug, comprising a fiber with a core-shell structure, wherein a core of the fiber comprises curcumin and a first spinnable polymer, and a shell of the fiber comprises polyethylene glycol and a second spinnable polymer; and in the shell, the polyethylene glycol and the second spinnable polymer have a mass ratio of not greater than 1:12;
wherein the core and the shell have a mass ratio of (13-21):13;

the shell has a thickness of 86 nm to 140 nm; and the hydrophilic fiber membrane with the sustained-release drug is prepared by a method comprising the following steps:

conducting coaxial electrospinning on a core spinning solution and a shell spinning solution to obtain the hydrophilic fiber membrane with the sustained-release drug; wherein the core spinning solution comprises the curcumin, the first spinnable polymer, and a first volatile organic solvent;

the shell spinning solution comprises the polyethylene glycol, the second spinnable polymer, and a second volatile organic solvent; and in the shell spinning solution, the polyethylene glycol and the second spinnable polymer have a mass ratio of not greater than 1:12;

wherein the coaxial electrospinning is further conducted using a third volatile organic solvent with the core spinning solution and the shell spinning solution; when the coaxial electrospinning is conducted, the core spinning solution, the shell spinning solution, and the third volatile organic solvent are arranged from inside to outside sequentially.

2. The hydrophilic fiber membrane according to claim 1, wherein the first spinnable polymer and the second spinnable polymer each are one selected from the group consisting of cellulose acetate, polycaprolactone, polylactic acid, gelatin, and nylon.

3. The hydrophilic fiber membrane according to claim 1, wherein in the core, the curcumin and the first spinnable polymer have a mass ratio of 1:(4-18).

4. The hydrophilic fiber membrane according to claim 2, wherein in the core, the curcumin and the first spinnable polymer have a mass ratio of 1:(4-18).

5. A preparation method of a hydrophilic fiber membrane with a sustained-release drug, the hydrophilic fiber comprising a fiber with a core-shell structure, wherein a core of the fiber comprises curcumin and a first spinnable polymer, and a shell of the fiber comprises polyethylene glycol and a second spinnable polymer; and in the shell, the polyethylene glycol and the second spinnable polymer have a mass ratio of not greater than 1:12; wherein the core and the shell have a mass ratio of (13-21):13; the shell has a thickness of 86 nm to 140 nm, the preparation method comprising the following steps:

conducting coaxial electrospinning on a core spinning solution and a shell spinning solution to obtain the hydrophilic fiber membrane with a sustained-release drug; wherein the core spinning solution comprises the curcumin, the first spinnable polymer, and a first volatile organic solvent;

the shell spinning solution comprises the polyethylene glycol, the second spinnable polymer, and a second volatile organic solvent; and in the shell spinning solution, the polyethylene glycol and the second spinnable polymer have a mass ratio of not greater than 1:12; and the coaxial electrospinning is further conducted using a third volatile organic solvent with the core spinning solution and the shell spinning solution; when the coaxial electrospinning is conducted, the core spinning solution, the shell spinning solution, and the third volatile organic solvent are arranged from inside to outside sequentially.

6. The preparation method according to claim 5, wherein the first spinnable polymer and the second spinnable polymer each are one selected from the group consisting of cellulose acetate, polycaprolactone, polylactic acid, gelatin, and nylon.

7. The preparation method according to claim 5, wherein in the core, the curcumin and the first spinnable polymer have a mass ratio of 1:(4-18).

8. The preparation method according to claim 5, wherein the core spinning solution has 1 g/L to 3 g/L of the curcumin and 12 g/L to 18 g/L of the first spinnable polymer by concentration.

9. The preparation method according to claim 5, wherein the first volatile organic solvent and the second volatile organic solvent each are a polar mixed solvent; and during the coaxial electrospinning, the first volatile organic solvent and the second volatile organic solvent each are added at a rate of 0.1 mL/h to 2 mL/h.

10. The preparation method according to claim 5, wherein during the coaxial electrospinning, the third volatile organic solvent is added at a rate of 0.1 mL/h to 2 mL/h.

11. A method for preparing a wound dressing, using the hydrophilic fiber membrane with a sustained-release drug according to claim 1.

* * * * *